US00PP11369P

United States Patent [19]

Zary

[11] Patent Number: Plant 11,369

[45] Date of Patent: May 2, 2000

[54] HYBRID TEA ROSE PLANT 'JACECOND'

[75] Inventor: Keith W. Zary, Thousand Oaks, Calif.

[73] Assignee: Bear Creek Gardens, Inc., Medford, Oreg.

[21] Appl. No.: 08/759,967

[22] Filed: Dec. 3, 1996

[51] Int. Cl.[7] ..... A01H 5/00

[52] U.S. Cl. ..... Plt./20

[58] Field of Search ..... Plt./20, 21

*Primary Examiner*—Howard J. Locker

*Attorney, Agent, or Firm*—Klarquist Sparkman Campbell Leigh & Whinston, LLP

[57] ABSTRACT

A new and distinct variety of rose plant of the hybrid tea class having high-centered red flowers presented singly (one to a stem), numerous thorns, vigorous, upright, well branched habit of growth, and dark green, leathery foliage.

1 Drawing Sheet

The present invention relates to a new and distinct variety of rose plant of the hybrid tea class which was originated by me by crossing the variety JACara, U.S. Plant Pat. No. 6,516, with the variety KORlingo, U.S. Plant Pat. No. 5,846.

The primary objective of this breeding was to produce a new rose variety having the vigorous, upright, well branched growth habit, clean healthy foliage and heavy flower production of the female parent combined with the well-formed high-centered blooms of the male parent. It was also hoped to obtain a flower color as close to KORlingo as possible. The objective was substantially achieved, along with other desirable improvements, as evidenced by the following unique combination of characteristics that are outstanding in the new variety and that distinguish it from its parents, as well as from all other varieties of which I am aware:

1. Very high-centered blooms;
2. Attractive red flower color;
3. Vigorous, upright, well branched habit of growth;
4. Dark green, leathery foliage;
5. Numerous thorns; and
6. Blooms presented singly.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—JACara.

*Pollen parent.*—KORlingo.

Classification:

*Botanical.*—Rosa hybrida.

*Commercial.*—Hybrid tea.

FLOWER

Observations made from specimens grown in a garden environment at Somis, Calif., in March through September, 1996.

Blooming habit: Recurrent.

Bud:

*Size.*—1¾ inches long when the petals start to unfurl.

*Form.*—The bud form is long, pointed ovoid.

*Color.*—When sepals first divide, bud color is Red Group 45A. When half blown, the upper sides of the petals are Red Group 45A; and the lower sides of the petals are Red Group 53C.

*Sepals.*—Color: Green Group 138B. Surface texture: Covered in fine hairs. There are three lightly appendaged sepals. There are two unappendaged sepals with hairy edges.

*Receptacle.*—Color: Green Group 141C. Shape: Funnel. Size: Medium (⅜ inch×⅜ inch). Surface: Smooth.

*Peduncle.*—Length: Short (1½ inches to 1¾ inches). Surface: Smooth with an occasional gland and some very small thorns. Color: Medium green and bronzy. Strength: Stiff, erect.

Bloom:

*Size.*—Medium. Average open size is 4 inches.

*Borne.*—Singly.

*Stems.*—Medium. Average length is about 16 inches to 20 inches.

*Form.*—When first open: High centered. Permanence: Outer petals curl back with some quilling.

*Petalage.*—Number of petals under normal conditions: 25 to 30.

*Color.*—The upper side of the petals is Red Group 45A. The reverse side of the petals is Red Group 53C. The base of each petal has a yellow (Yellow Group 6A) half moon (⅛ inch×⅛ inch) at the point of attachment. The major color on the upper side is Red Group 45A.

*Variegations.*—Occasional white streak on the guard petals.

*Discoloration.*—The general tonality at the end of the first day: No change. At the end of the third day: No change. By day 4 or 5, there is a gradual lightening of color intensity to Red Group 45C.

*Fragrance.*—Slight.

Petals:

*Texture.*—Thick.

*Shape.*—Round.

*Form.*—Tips slightly recurved, edges slightly quilled.

*Arrangement.*—Imbricated, with few petaloids in the center.

*Persistence.*—Drop off cleanly.

*Lastingness.*—On the plant: Long (6 or 7 days). As a cut flower: Long (9 or 10 days.

Reproductive Parts:

*Anthers.*—Size: Medium. Quantity: Many. Color: Yellow. Arrangement: Regular around styles.

*Filaments.*—Color: Reddish brown.

*Pollen.*—Color: Gold Yellow.

*Styles.*—Color: Red.

*Stigmas.*—Color: Greenish White.

Form: Bush.

Growth: Vigorous; upright; branching; height in California at one year without pruning is 5 feet tall by 4 feet wide.

Foliage: Number of leaflets on normal mid-stem leaves: 5.

*Size.*—Medium (5 inches×4 inches).

*Quantity.*—Abundant.

*Color.*—New foliage: Red Purple Group 183A on both surfaces. Old foliage: Upper surface Green Group 139A. Lower surface Green Group 139C.

Leaflets:

*Shape.*—Pointed oval.

*Texture.*—Upper side: Leathery, glossy.

*Edge.*—Serrated.

*Serration.*—Single, small.

*Petiole rachis.*—Color: Reddish.

*Petiole underside.*—Smooth with occasional prickles.

*Stipules.*—Medium (⅜ inch), serrated.

*Disease resistance.*—Resistant to mildew and rust under normal growing conditions at Somis, California.

Wood:

*New wood.*—Color: Light green. Bark: Smooth.

*Old wood.*—Color: Green. Bark: Smooth.

Prickles:

*Quantity.*—On main canes from base: Many. On laterals from main canes: Many.

*Form.*—Medium (⅜ inch to ¼ inch), hooked downward.

*Color when young.*—Red.

Small prickles:

*Quantity.*—On main stalks: Few. On laterals: Few.

*Color.*—Brown.

I claim:

1. A new and distinct variety of rose plant of the hybrid tea class, substantially as herein shown and described, characterized particularly as to novelty by the unique combination of its high-centered red flowers presented singly (one to a stem), its numerous thorns, its vigorous, upright, well branched habit of growth, and its dark green leathery foliage.

* * * * *

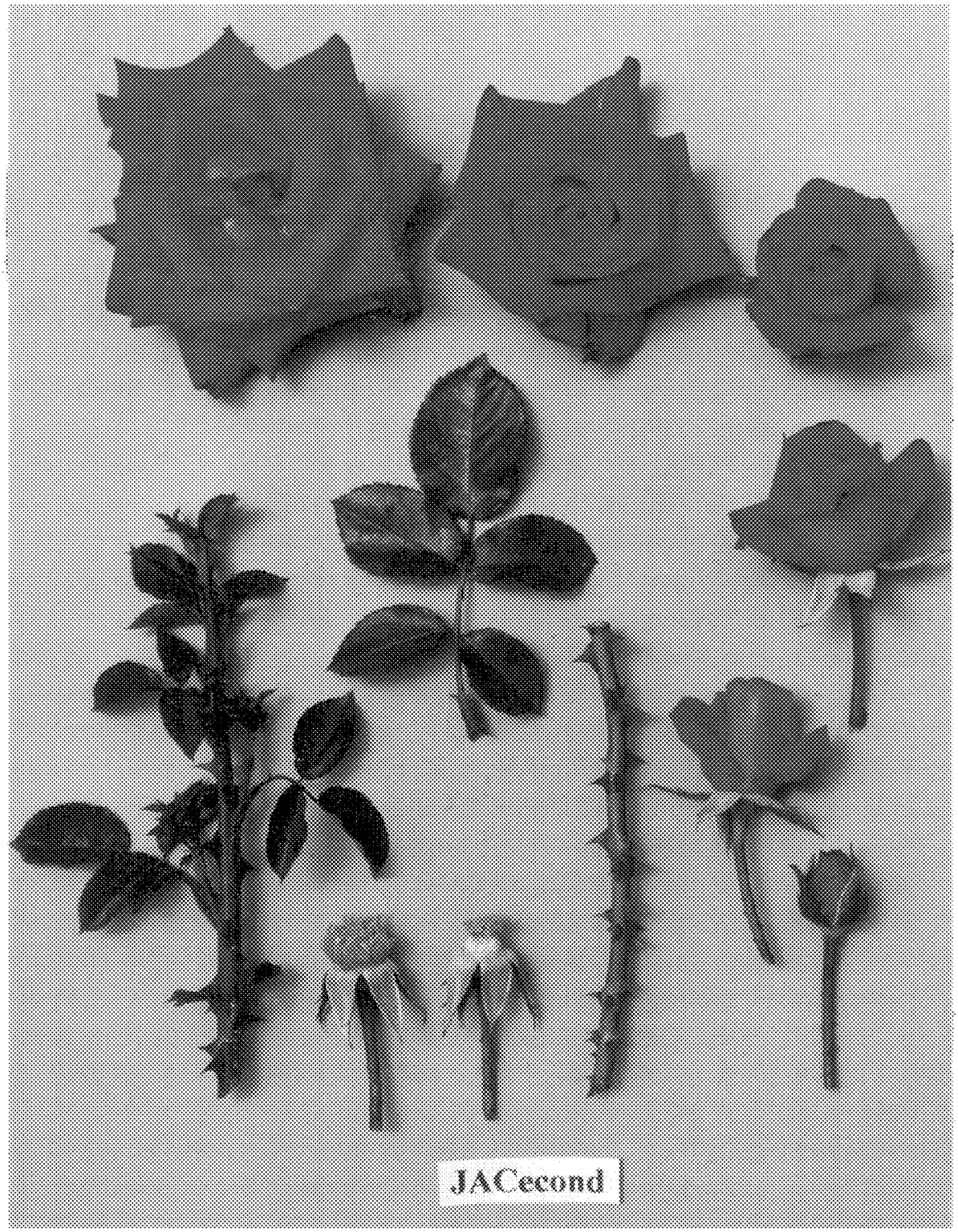
JACecond

UNITED STATES PATENT AND TRADEMARK OFFICE

CERTIFICATE OF CORRECTION

PATENT NO. : PP11,369
DATED : May 2, 2000
INVENTOR(S) : Keith W. Zary, Ph.D.

It is certified that error appears in the above-identified patent and that said Letters Patent is hereby corrected as shown below:

Column 1,
Line 17, reads "Attractive red". It should read --Attractive near red--.

Column 2,
Line 18, reads "Medium green and bronzy". It should read --Medium green--.

Signed and Sealed this

Seventeenth Day of July, 2001

*Attest:*

Nicholas P. Godici

NICHOLAS P. GODICI

*Attesting Officer*

*Acting Director of the United States Patent and Trademark Office*